United States Patent [19]

Shiraishi et al.

[11] Patent Number: 4,971,996

[45] Date of Patent: Nov. 20, 1990

[54] HYDROXYSTYRENE COMPOUNDS WHICH ARE USEFUL AS TYROSINE KINASE INHIBITORS

[75] Inventors: Tadayoshi Shiraishi, Takasago; Keiji Kameyama; Takeshi Domoto, both of Kakogawa; Naohiro Imai; Yoshio Shimada, both of Kakogawa; Yutaka Ariki, Himeji; Kazunori Hosoe; Masaji Kawatsu, both of Takasago; Ikuo Katsumi; Takayoshi Hidaka, both of Kobe; Kiyoshi Watanabe, Akashi, all of Japan

[73] Assignee: Kanegafuchi Kagaku Kogyo Kabushiki Kaisha, Osaka, Japan

[21] Appl. No.: 283,992

[22] PCT Filed: Mar. 10, 1988

[86] PCT No.: PCT/JP88/00254

§ 371 Date: Nov. 10, 1988

§ 102(e) Date: Nov. 10, 1988

[87] PCT Pub. No.: WO88/07035

PCT Pub. Date: Sep. 22, 1988

[30] Foreign Application Priority Data

Mar. 11, 1987 [JP] Japan .................. 62-55965
Mar. 11, 1987 [JP] Japan .................. 62-55966
Mar. 12, 1987 [JP] Japan .................. 62-57256

[51] Int. Cl.$^5$ .................. A61K 31/275; C07C 121/75
[52] U.S. Cl. .................. 514/521; 558/401
[58] Field of Search .................. 558/401; 514/523, 521

[56] References Cited

U.S. PATENT DOCUMENTS

| Re. 29,467 | 11/1977 | Nussim et al. | 558/401 |
|---|---|---|---|
| 3,912,519 | 10/1975 | Takagi et al. | 106/15 |
| 4,594,460 | 6/1986 | Mignami et al. | 568/794 |

FOREIGN PATENT DOCUMENTS

| 0057882 | 8/1982 | European Pat. Off. |
|---|---|---|
| 0154528 | 9/1985 | European Pat. Off. |
| 0204964 | 12/1986 | European Pat. Off. |
| 0211363 | 2/1987 | European Pat. Off. |
| 2258239 | 6/1973 | Fed. Rep. of Germany |
| 49-103929 | 10/1974 | Japan |
| 58-79920 | 5/1983 | Japan |
| 60-215636 | 10/1985 | Japan |
| 60-237033 | 11/1985 | Japan |
| 62-39522 | 2/1987 | Japan |
| 62-39523 | 2/1987 | Japan |
| 2039558 | 2/1987 | Japan .................. 558/401 |
| 62-111962 | 5/1987 | Japan |
| 1406307 | 9/1975 | United Kingdom |

OTHER PUBLICATIONS

Chemical Abstracts, vol. 106, No. 25, 22nd Jun. 1989, p. 661, abstract No. 213918z, Columbus, Ohio.

Primary Examiner—Mary C. Lee
Assistant Examiner—Zinna Northington-Davis
Attorney, Agent, or Firm—Armstrong, Nikaido, Marmelstein, Kubovcik & Murray

[57] ABSTRACT

A hydroxystyrene derivative represented by the formula (I):

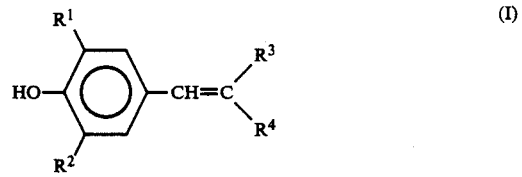

wherein when $R^1$ and $R^2$: phenyl group, benzyl group or phenethyl group, or $R^1$: $R^5O-$ ($R^5$: H, a $C_1$ to $C_5$ alkyl group or benzyl group) and $R^2$: benzyl group or $PhSCH_2$, $R^3$ and $R^4$ are taken together to represent $-CONH-CS-S-$,

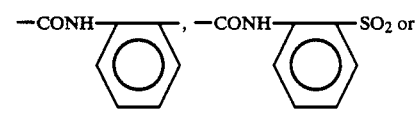

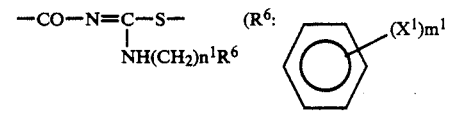

($X^1$: H, a halogen, methyl group, ethyl group, $R^7O-$ ($R^7$: methyl or ethyl group), nitro group, aminosulfonyl group or amino group, $m^1$: 1 or 2), pyridyl group, furyl group or thienyl group, $n^1$: an integer of 0 to 3); when $R^1$ and $R^2$: phenyl group, benzyl group or phenethyl group, or $R^1$: $R^5O-$ ($R^5$: as defined above) and $R^2$: benzyl group, $R^3$: cyano group and $R^4$: a carbamoyl group, or $R^3$ and $R^4$ are taken together to represent $-CO-Y-CH_2CH_2-$ (Y: O or $-NH-$) or $$-CO-N-NH-CO-;$$
$$\phantom{-CO-N}|$$
$$\phantom{-CO-N-NH-CO}Ph$$

and when $R^1$ and $R^2$: a $C_1$ to $C_3$ alkyl group, $R^3$ and $R^4$ are taken together to represent

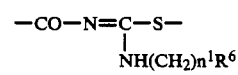

($n^1$, $R^6$: as defined above), or a salt thereof. The hydroxystyrene derivative or a salt thereof is a compound which is useful as an active ingredient of an antiallergic agent, a 5-lipoxygenase inhibiting agent, an antibacterial agent, a tryosine kinase inhibiting agent, an ultraviolet absorber or a reverse transcriptase inhibiting agent, and also is useful as an intermediate for preparing various organic compounds.

3 Claims, No Drawings

HYDROXYSTYRENE COMPOUNDS WHICH ARE USEFUL AS TYROSINE KINASE INHIBITORS

DESCRIPTION

1. Technical Field

The present invention relates to a novel hydroxystyrene derivative or a salt thereof, which has antiallergic activity, 5-lipoxygenase inhibiting activity, antibacterial activity, tyrosine kinase inhibiting activity, ultraviolet (hereinafter referred to as "UV") absorbing activity and reverse transcriptase inhibiting activity and is useful as an intermediate for preparing various organic compounds, and relates to an antiallergic agent, a 5-lipoxygenase inhibiting agent, an antibacterial agent, a tyrosine kinase inhibiting agent, an UV absorber and a reverse transcriptase inhibiting agent containing the same as an active ingredient.

2. Background Art

The compound of the present invention is a novel compound which has not yet been reported in a literature and is first synthesized by the present inventors.

3. Disclosure of the Invention

It has now been found that a novel hydroxystyrene derivative of the present invention is a useful intermediate for preparing various organic compounds and has itself antiallergic activity, 5-lipoxygenase inhibiting activity, antibacterial activity, tyrosine kinase inhibiting activity, UV absorbing activity and reverse transcriptase inhibiting activity.

In accordance with the present invention, there is provided a hydroxystyrene derivative represented by the formula (I):

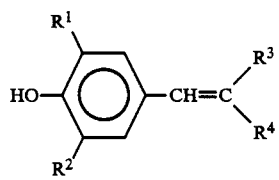

(I)

wherein when $R^1$ and $R^2$ are the same or different and each is phenyl group, benzyl group or phenethyl group, or $R^1$ is a group having the formula: $R^5O-$ in which $R^5$ is hydrogen atom, an alkyl group having 1 to 5 carbon atoms or benzyl group and $R^2$ is benzyl group or a group of $PhSCH_2$ in which Ph is phenyl group, hereinafter the same, $R^1$ and $R^4$ are taken together to represent a group having the formula: $-CONH-CS-S-$, a group having the formula:

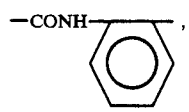

a group having the formula:

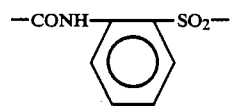

or a group having the formula:

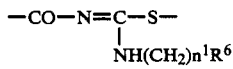

in which
$R^6$ is a group having the formula:

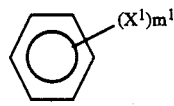

in which $X^1$ is hydrogen atom, a halogen atom, methyl group, ethyl group, an alkoxyl group having the formula: $R^7O-$ (in which $R^7$ is methyl group or ethyl group), nitro group, aminosulfonyl group or amino group, and $m^1$ is 1 or 2], pyridyl group, furyl group or thienyl group, and $n^1$ is 0 or an integer of 1 to 3; when $R^1$ and $R^2$ are the same or different and each is phenyl group, benzyl group or phenethyl group, or $R^1$ is a group having the formula: $R^5O-$ in which $R^5$ is as defined above, and $R^2$ is benzyl group, $R^3$ is cyano group and $R^4$ is carbamoyl group, or $R^3$ and $R^4$ are taken together to represent a group having the formula: $-CO-Y-CH_2CH_2-$ in which Y is oxygen atom or $-NH-$, or a group having the formula:

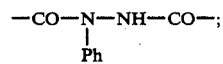

and when $R^1$ and $R^2$ are the same or different and each is an alkyl group having 1 to 3 carbon atoms, $R^3$ and $R^4$ are taken together to represent a group having the formula:

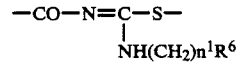

in which $n^1$ and $R^6$ are as defined above, or a salt thereof.

The compound having the formula (I) of the present invention can form a salt with a base or an acid. The salt of the present invention may be any which can be formed from the compound of the present invention and the base or the acid.

Examples of the salt with the base are, for instance, (1) a salt with metal, especially an alkali metal salt, an alkaline earth metal salt and a salt with aluminum; (2) an ammonium salt; and (3) an amine salt, especially a salt with methylamine, ethylamine, diethylamine, triethylamine, pyrrolidine, piperidine, morpholine, hexamethyleneimine, aniline or pyridine, and the like.

Examples of the salt with the acid are, for instance, (1) a salt with an inorganic acid, especially a salt with hydrochloric acid, sulfuric acid, phosphoric acid, nitric acid or carbonic acid; (2) a salt with an organic acid, especially a salt with a carboxylic acid such as formic acid, acetic acid, propionic acid, succinic acid, oxalic acid, tartaric acid, maleic acid, lactic acid, benzoic acid, anthranilic acid or salicylic acid; a salt with a sulfonic acid such as p-toluenesulfonic acid or methanesulfonic acid; a salt with an amino acid such as glycine, methionine or lysine; and the like.

When the salts are employed for the antiallergic agent, the 5-lipoxygenase inhibiting agent, the antibacterial agent, the tyrosine kinase inhibiting agent, the UV absorber or the reverse transcriptase inhibiting agent, the pharmaceutically acceptable salts should be employed.

As typical examples of the compounds of the invention, the compounds (1) to (45) are shown in Table 1 by showing the groups $R^1$, $R^2$, $R^3$ and $R^4$ in the formula (I), and further, exemplifying the group $R^6$ and $n^1$ in case that $R^3$ and $R^4$ are taken together to represent a group having the formula:

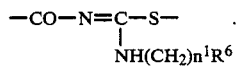

Also, the molecular formula, molecular weight, melting point, and data of elementary analysis of each compound of (1) to (45) are shown in Table 1. The results of $^1$H-NMR spectrum analysis and IR spectrum analysis of the compounds (1) to (45) are shown in Table 2.

TABLE 1

| Compound No. | $R^1$ | $R^2$ | $R^3$ | $R^4$ | $R^6$ | Molecular formula (Molecular weight) | Melting point (°C.) | C Found (%) | C Calcd. (%) | H Found (%) | H Calcd. (%) | N Found (%) | N Calcd. (%) |
|---|---|---|---|---|---|---|---|---|---|---|---|---|---|
| 1 | Ph | Ph | —CONH—CS—S— | | — | $C_{22}H_{15}NO_2S_2$ (389.50) | 220 to 222 | 68.13 | 67.84 | 3.95 | 3.88 | 3.81 | 3.60 |
| 2 | $PhCH_2$ | $PhCH_2$ | —CONH—CS—S— | | — | $C_{24}H_{19}NO_2S_2$ (417.55) | 223 to 225 | 69.37 | 69.04 | 4.44 | 4.59 | 3.05 | 3.35 |
| 3 | Ph | Ph | —CONH— |  | — | $C_{27}H_{19}NO_2$ (389.43) | 223 to 225 | 83.49 | 83.27 | 5.03 | 4.92 | 3.89 | 3.60 |
| 4 | $PhCH_2$ | $PhCH_2$ | —CONH— |  | — | $C_{29}H_{23}NO_2$ (417.48) | 179 to 181 | 83.36 | 83.43 | 5.60 | 5.55 | 3.54 | 3.36 |
| 5 | $PhCH_2$ | $PhCH_2$ | —CONH— | $SO_2$— | — | $C_{29}H_{23}NO_4S$ (481.57) | 208 to 209 | 72.68 | 72.33 | 4.77 | 4.81 | 3.18 | 2.91 |
| 6 | $C_2H_5O$ | $PhSCH_2$ | —CONH—CS—S— | | — | $C_{19}H_{17}NO_3S_3$ (403.54) | 190 to 191 | 56.37 | 56.55 | 4.44 | 4.25 | 3.58 | 3.47 |
| 7 | HO | $PhSCH_2$ | —CONH—CS—S— | | — | $C_{17}H_{13}NO_3S_3$ (375.49) | 189 to 192 | 54.62 | 54.38 | 3.61 | 3.49 | 3.55 | 3.73 |
| 8 | $PhCH_2O$ | $PhSCH_2$ | —CONH—CS—S— | | — | $C_{24}H_{19}NO_3S_3$ (465.61) | 161 to 163 | 62.08 | 61.91 | 3.99 | 4.11 | 2.65 | 3.01 |
| 9 | $n-C_4H_9O$ | $PhSCH_2$ | —CONH—CS—S— | | — | $C_{21}H_{21}NO_3S_3$ (431.60) | 189 to 190 | 58.08 | 58.44 | 5.02 | 4.90 | 3.63 | 3.25 |
| 10 | $n-C_4H_9O$ | $PhCH_2$ | —CONH—CS—S— | | — | $C_{21}H_{21}NO_3S_2$ (399.53) | 210 to 212 | 63.37 | 63.13 | 5.18 | 5.30 | 3.75 | 3.51 |
| 11 | HO | $PhSCH_2$ | —CONH— |  | — | $C_{22}H_{17}NO_3S$ (375.45) | 190 to 191 | 70.63 | 70.39 | 4.68 | 4.57 | 3.39 | 3.73 |
| 12 | $PhCH_2O$ | $PhSCH_2$ | —CONH— |  | — | $C_{29}H_{23}NO_3S$ (465.57) | 155 to 158 | 74.56 | 74.82 | 5.13 | 4.98 | 3.37 | 3.01 |

TABLE 1-continued

| Compound No. | $R^1$ | $R^2$ | $R^3$ $R^4$ | $R^6$ | $n^1$ | Molecular formula (Molecular weight) | Melting point (°C.) | C Found (%) | C Calcd. (%) | H Found (%) | H Calcd. (%) | N Found (%) | N Calcd. (%) |
|---|---|---|---|---|---|---|---|---|---|---|---|---|---|
| 13 | $CH_3O$ | $PhCH_2$ | —CONH—Ph | — | — | $C_{23}H_{19}NO_3$ (357.39) | 228 to 231 | 77.30 | 77.30 | 5.59 | 5.36 | 4.05 | 3.92 |
| 14 | $n\text{-}C_4H_9O$ | $PhCH_2$ | —CONH—Ph | — | — | $C_{26}H_{25}NO_3$ (399.49) | 185 to 186 | 78.42 | 78.17 | 6.12 | 6.31 | 3.82 | 3.51 |
| 15 | Ph | Ph | CN, $CONH_2$ | — | — | $C_{22}H_{16}N_2O_2$ (340.36) | 179 to 181 | 77.81 | 77.63 | 4.71 | 4.74 | 8.51 | 8.23 |
| 16 | $PhCH_2$ | $PhCH_2$ | CN, $CONH_2$ | — | — | $C_{24}H_{20}N_2O_2$ (368.42) | 150 to 158 | 78.01 | 78.24 | 5.31 | 5.47 | 7.98 | 7.60 |
| 17 | $PhCH_2$ | $PhCH_2$ | $-COOCH_2CH_2-$ | — | — | $C_{25}H_{22}O_3$ (370.45) | 167 to 168 | 80.92 | 81.05 | 5.97 | 5.99 | — | — |
| 18 | $PhCH_2$ | $PhCH_2$ | $-CONHCH_2CH_2-$ | — | — | $C_{25}H_{23}NO_2$ (369.46) | 157 to 159 | 81.45 | 81.26 | 6.46 | 6.28 | 3.50 | 3.79 |
| 19 | Ph | Ph | —CON—NHCO—<br>    \|<br>    Ph | — | — | $C_{28}H_{20}N_2O_3$ (432.48) | 231 to 232 | 77.43 | 77.76 | 4.49 | 4.66 | 6.61 | 6.48 |
| 20 | $PhCH_2$ | $PhCH_2$ | —CON—NHCO—<br>    \|<br>    Ph | — | — | $C_{30}H_{24}N_2O_3$ (460.51) | 202 to 203 | 78.13 | 78.24 | 5.16 | 5.25 | 6.32 | 6.08 |
| 21 | $C_2H_5O$ | $PhCH_2$ | CN, $CONH_2$ | — | — | $C_{19}H_{18}N_2O_3$ (322.35) | 173 to 174 | 70.56 | 70.80 | 5.47 | 5.63 | 8.80 | 8.69 |
| 22 | $CH_3O$ | $PhCH_2$ | CN, $CONH_2$ | — | — | $C_{18}H_{16}N_2O_3$ (308.32) | 208 to 209 | 70.02 | 70.12 | 5.45 | 5.23 | 9.21 | 9.09 |
| 23 | HO | $PhCH_2$ | CN, $CONH_2$ | — | — | $C_{17}H_{14}N_2O_3$ (294.30) | 266 to 268 | 69.62 | 69.38 | 4.96 | 4.80 | 9.31 | 9.52 |
| 24 | HO | $PhCH_2$ | —CON—NHCO—<br>    \|<br>    Ph | — | — | $C_{23}H_{18}N_2O_4$ (386.41) | 252 to 255 | 71.25 | 71.49 | 4.57 | 4.70 | 7.59 | 7.25 |
| 25 | Ph | Ph | $-CO-N=C-S-$<br>           \|<br>           $NH(CH_2)_{n^1}R^6$ | Ph | 1 | $C_{29}H_{22}N_2O_2S$ (462.57) | 257 to 259 | 75.18 | 75.31 | 4.63 | 4.80 | 5.78 | 6.06 |
| 26 | $PhCH_2$ | $PhCH_2$ | $-CO-N=C-S-$<br>           \|<br>           $NH(CH_2)_{n^1}R^6$ | Ph | 1 | $C_{31}H_{26}N_2O_2S$ (490.63) | 245 to 246 | 75.67 | 75.90 | 5.21 | 5.34 | 5.99 | 5.71 |

TABLE 1-continued

| Compound No. | $R^1$ | $R^2$ | $R^3$ $R_4$ | $R^6$ | $n^1$ | Molecular formula (Molecular weight) | Melting point (°C.) | C Found (%) | C Calcd. (%) | H Found (%) | H Calcd. (%) | N Found (%) | N Calcd. (%) |
|---|---|---|---|---|---|---|---|---|---|---|---|---|---|
| 27 | HO | PhSCH$_2$ | $-CO-N=C-S-$<br>$\quad\quad\quad\;\;\|$<br>$\quad\quad\quad\;\;NH(CH_2)n^1R^6$ |  | 1 | $C_{22}H_{18}N_2O_4S_2$ (438.52) | 244 to 246 | 60.54 | 60.27 | 4.27 | 4.14 | 6.02 | 6.39 |
| 28 | $C_2H_5O$ | PhSCH$_2$ | $-CO-N=C-S-$<br>$\quad\quad\quad\;\;\|$<br>$\quad\quad\quad\;\;NH(CH_2)n^1R^6$ | Ph | 1 | $C_{26}H_{24}N_2O_3S_2$ (476.62) | 194 to 196 | 65.18 | 65.52 | 5.01 | 5.08 | 5.53 | 5.88 |
| 29 | $n-C_4H_9O$ | PhSCH$_2$ | $-CO-N=C-S-$<br>$\quad\quad\quad\;\;\|$<br>$\quad\quad\quad\;\;NH(CH_2)n^1R^6$ | Ph | 1 | $C_{28}H_{28}N_2O_3S_2$ (504.67) | 175 to 176 | 66.87 | 66.65 | 5.63 | 5.59 | 5.84 | 5.55 |
| 30 | $n-C_4H_9O$ | PhCH$_2$ | $-CO-N=C-S-$<br>$\quad\quad\quad\;\;\|$<br>$\quad\quad\quad\;\;NH(CH_2)n^1R^6$ | Ph | 1 | $C_{28}H_{28}N_2O_3S$ (472.61) | 144 to 145 | 71.41 | 71.17 | 6.08 | 5.97 | 5.66 | 5.93 |
| 31 | PhCH$_2$O | PhSCH$_2$ | $-CO-N=C-S-$<br>$\quad\quad\quad\;\;\|$<br>$\quad\quad\quad\;\;NH(CH_2)n^1R^6$ | 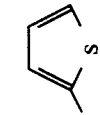 | 1 | $C_{29}H_{24}N_2O_3S_3$ (544.71) | 152 to 153 | 64.23 | 63.95 | 4.57 | 4.44 | 4.85 | 5.14 |
| 32 | $i-C_3H_7$ | $i-C_3H_7$ | $-CO-N=C-S-$<br>$\quad\quad\quad\;\;\|$<br>$\quad\quad\quad\;\;NH(CH_2)n^1R^6$ | Ph | 0 | $C_{22}H_{24}N_2O_2S$ (380.50) | 213 to 216 | 69.31 | 69.45 | 6.30 | 6.36 | 7.63 | 7.36 |
| 33 | $i-C_3H_7$ | $i-C_3H_7$ | $-CO-N=C-S-$<br>$\quad\quad\quad\;\;\|$<br>$\quad\quad\quad\;\;NH(CH_2)n^1R^6$ | Ph | 1 | $C_{23}H_{26}N_2O_2S$ (394.53) | 180 to 183 | 70.18 | 70.03 | 6.58 | 6.64 | 7.27 | 7.10 |
| 34 | $i-C_3H_7$ | $i-C_3H_7$ | $-CO-N=C-S-$<br>$\quad\quad\quad\;\;\|$<br>$\quad\quad\quad\;\;NH(CH_2)n^1R^6$ | Ph | 2 | $C_{24}H_{28}N_2O_2S$ (408.55) | 144 to 146 | 70.43 | 70.56 | 7.02 | 6.91 | 7.08 | 6.86 |
| 35 | $i-C_3H_7$ | $i-C_3H_7$ | $-CO-N=C-S-$<br>$\quad\quad\quad\;\;\|$<br>$\quad\quad\quad\;\;NH(CH_2)n^1R^6$ | 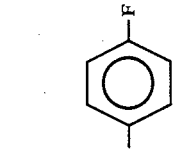 | 1 | $C_{23}H_{25}N_2O_2SF$ (412.52) | 172 to 175 | 66.76 | 66.98 | 6.24 | 6.11 | 6.99 | 6.79 |
| 36 | $i-C_3H_7$ | $i-C_3H_7$ | $-CO-N=C-S-$<br>$\quad\quad\quad\;\;\|$<br>$\quad\quad\quad\;\;NH(CH_2)n^1R^6$ | 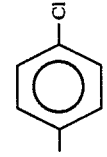 | 1 | $C_{23}H_{25}N_2O_2SCl$ (428.97) | 184 to 186 | 64.56 | 64.40 | 5.98 | 5.87 | 6.77 | 6.53 |

TABLE 1-continued

| Compound No. | R¹ | R² | R³ R⁴ | R⁶ | n¹ | Molecular formula (Molecular weight) | Melting point (°C.) | Elementary analysis |||||| 
|---|---|---|---|---|---|---|---|---|---|---|---|---|---|
| | | | | | | | | C Found (%) | C Calcd. (%) | H Found (%) | H Calcd. (%) | N Found (%) | N Calcd. (%) |
| 37 | i-C₃H₇ | i-C₃H₇ | —CO—N=C—S— / NH(CH₂)n¹R⁶ | 3,4-diCl-C₆H₃ | 1 | C₂₃H₂₄N₂O₂SCl₂ (463.41) | 140 (decomp.) | 59.37 | 59.61 | 5.43 | 5.22 | 5.68 | 6.05 |
| 38 | i-C₃H₇ | i-C₃H₇ | —CO—N=C—S— / NH(CH₂)n¹R⁶ | 4-OCH₃-C₆H₄ | 1 | C₂₄H₂₈N₂O₃S (424.55) | 169 to 174 | 67.52 | 67.90 | 6.83 | 6.65 | 7.03 | 6.05 |
| 39 | i-C₃H₇ | i-C₃H₇ | —CO—N=C—S— / NH(CH₂)n¹R⁶ | 4-CH₃-C₆H₄ | 1 | C₂₄H₂₈N₂O₂S (408.55) | 155 to 157 | 70.80 | 70.56 | 6.99 | 6.91 | 6.47 | 6.86 |
| 40 | i-C₃H₇ | i-C₃H₇ | —CO—N=C—S— / NH(CH₂)n¹R⁶ | 4-NO₂-C₆H₄ | 1 | C₂₃H₂₅N₃O₄S (439.53) | 128 to 131 | 62.62 | 62.86 | 5.61 | 5.73 | 9.31 | 9.56 |
| 41 | i-C₃H₇ | i-C₃H₇ | —CO—N=C—S— / NH(CH₂)n¹R⁶ | 4-SO₂NH₂-C₆H₄ | 1 | C₂₃H₂₇N₃O₄S₂ (478.60) | 165 to 169 | 58.72 | 58.34 | 5.96 | 5.75 | 8.68 | 8.88 |
| 42 | i-C₃H₇ | i-C₃H₇ | —CO—N=C—S— / NH(CH₂)n¹R⁶ | 4-NH₂-C₆H₄ | 1 | C₂₃H₂₇N₃O₂S (409.55) | 160 (decomp.) | 67.63 | 67.46 | 6.53 | 6.65 | 10.57 | 10.26 |
| 43 | i-C₃H₇ | i-C₃H₇ | —CO—N=C—S— / NH(CH₂)n¹R⁶ | 2-furyl | 1 | C₂₁H₂₄N₂O₃S (384.48) | 170 to 180 | 65.38 | 65.61 | 6.37 | 6.29 | 7.41 | 7.29 |
| 44 | i-C₃H₇ | i-C₃H₇ | —CO—N=C—S— / NH(CH₂)n¹R⁶ | 2-thienyl | 1 | C₂₁H₂₄N₂O₂S₂ (400.55) | 180 to 183 | 63.31 | 62.99 | 6.18 | 6.04 | 6.71 | 7.00 |

TABLE 1-continued
| Compound No. | R¹ | R² | R³ R⁴ | R⁶ | n¹ | Molecular formula (Molecular weight) | Melting point (°C.) | Elementary analysis | | | | | |
|---|---|---|---|---|---|---|---|---|---|---|---|---|---|
| | | | | | | | | C | | H | | N | |
| | | | | | | | | Found (%) | Calcd. (%) | Found (%) | Calcd. (%) | Found (%) | Calcd. (%) |
| 45 | i-$C_3H_7$ | i-$C_3H_7$ | $-CO-N=C-S-$<br>$\quad\quad\quad\quad\quad\mid$<br>$\quad\quad\quad\quad NH(CH_2)n^1R^6$ |  | 1 | $C_{22}H_{25}N_3O_2S$<br>(395.52) | 110 to 113 | 66.53 | 66.82 | 6.49 | 6.37 | 10.98 | 10.63 |

TABLE 2

| Compound No. | $^1$H-NMR spectrum δ (ppm) | IR spectrum (cm$^{-1}$) |
|---|---|---|
| 1 | CDCl$_3$/DMSO-d$_6$ = 1/1;7.3–7.7(13H,m), 9.01(1H,br), 13.4(1H,br) | KBr; 3540, 3150, 3050, 1700, 1590 |
| 2 | CDCl$_3$/DMSO-d$_6$ = 1/1;4.03(4H,s), 7.0–7.4(13H,m), 9.27(1H,br), 13.55(1H,br) | KBr; 3330, 3300, 1680, 1570 |
| 3 | CDCl$_3$/DMSO-d$_6$ = 1/1;6.7–7.8(16H,m), 8.33(1H,s), 8.6(1H,br), 10.4(1H,br) | KBr; 3550, 3180, 3050, 1695, 1620, 1590 |
| 4 | CDCl$_3$/DMSO-d$_6$ = 1/1;4.05(4H,s), 6.5–7.3(16H,m), 7.45(1H,s), 9.0(1H,br), 10.2(1H,br) | KBr; 3380, 3200, 1685, 1585 |
| 5 | CDCl$_3$/DMSO-d$_6$ = 1/1;3.97(4H,s), 7.1–7.8(16H,m), 7.75(1H,s), 9.5(1H,br) | KBr; 3450, 3200, 3060, 1680, 1600 |
| 6 | CDCl$_3$/DMSO-d$_6$ = 2/1;1.40(3H,t), 4.10(2H, q), 4.16(2H,s), 4.70(2H,d), 7.0–7.7(15H, m), 9.1–9.6(1H,br), 9.7–10.0(1H,br) | |
| 7 | CDCl$_3$/DMSO-d$_6$ = 1/1;4.15(2H,s), 6.9 (2H,s), 7.0–8.6(8H,m), 10.0(2H,br) | KBr; 3440, 3260, 1670, 1575 |
| 8 | CDCl$_3$/DMSO-d$_6$ = 1/1;4.18(2H,s), 5.18 (2H,s), 6.8–7.6(13H,m), 9.7(1H,br) | KBr; 3520, 3120, 3050, 2850, 1675, 1570 |
| 9 | CDCl$_3$/DMSO-d$_6$ = 1/1;0.98(3H,t), 1.2–1.9(4H,m), 4.05(2H,t), 4.17(2H,s), 6.97(2H,s), 7.0–7.3(5H,m), 7.42(1H,s), 9.45(1H,br), 13.4(1H,br) | KBr; 3480, 3130, 3050, 2850, 1675, 1570 |
| 10 | CDCl$_3$/DMSO-d$_6$ = 1/1;0.95(3H,t), 1.3–2.0(4H,m), 3.93(2H,s), 4.02(2H,t), 6.8–7.4(7H,m), 7.45(1H,s), 9.28(1H,br) | KBr; 3480, 3130, 3020, 2950, 2850, 1685, 1570 |
| 11 | CDCl$_3$/DMSO-d$_6$ = 1/1;4.19(2H,s), 6.7–7.8(12H,m), 9.3(2H,br), 10.3(1H,br) | KBr; 3420, 3180, 1705, 1590 |
| 12 | CDCl$_3$/DMSO-d$_6$ = 1/1;4.22(2H,s), 5.25 (2H,s), 6.7–7.7(16H,m), 8.87(1H,d), 9.3(1H,br), 10.3(1H,br) | KBr; 3505, 3150, 3080, 3050, 3020, 1670, 1615, 1580 |
| 13 | CDCl$_3$/DMSO-d$_6$ = 1/1;3.97(3H,s), 4.00 (2H,s), 6.7–7.6(11H,m), 8.77(1H,d), 9.2(1H,br), 10.4(1H,br) | KBr; 3400, 3170, 3060, 1690, 1620, 1610, 1580 |
| 14 | CDCl$_3$/DMSO-d$_6$ = 1/1;0.94(3H,t), 1.3–1.9(4H,m), 3.94(2H,s), 4.00(2H,t), 6.5–7.5(12H,m), 8.9(1H,br), 10.4(1H,br) | KBr; 3160, 3130, 3060, 3020, 2950, 1685, 1610 |
| 15 | CDCl$_3$/DMSO-d$_6$ = 1/1;7.3–7.8(12H,m), 7.85(2H,s), 8.15(1H,s), 9.25(1H,s) | KBr; 3500, 3475, 3300, 3200, 2205, 1710, 1580 |
| 16 | CDCl$_3$/DMSO-d$_6$ = 1/1;4.00(4H,s), 7.1–7.3(10H,m), 7.4(2H,br), 7.57(2H,s), 7.90(1H,s), 9.5(1H,br) | KBr; 3400, 3320, 2205, 1660, 1565 |
| 17 | CDCl$_3$/DMSO-d$_6$ = 1/1;2.93(2H,t-d), 4.00 (4H,s), 4.30(2H,t), 7.0–7.3(13H,m), 9.0(1H,br) | KBr; 3360, 1720, 1645, 1590 |
| 18 | CDCl$_3$/DMSO-d$_6$ = 1/1;2.77(2H,m), 3.30 (2H,m), 3.97(4H,s), 6.8–7.5(13H,m), 7.8(1H,br), 8.8(1H,br) | KBr; 3400, 3200, 2900, 1685, 1640, 1600, 1580 |
| 19 | CDCl$_3$/DMSO-d$_6$ = 1/1;7.0–8.0(16H,m), 8.48(1H,s), 8.53(1H,s), 9.3(1H,br) | KBr; 3530, 3220, 3080, 1720, 1660, 1620, 1570 |
| 20 | CDCl$_3$/DMSO-d$_6$ = 1/1;4.00(4H,s), 7.0–7.9(16H,m), 8.3(1H,s), 8.35(1H,s), 9.8(1H,br) | KBr; 3150, 3060, 3020, 1700, 1655, 1620, 1570 |
| 21 | CDCl$_3$/DMSO-d$_6$ = 1/1;1.43(3H,t), 3.97 (2H,s), 4.12(2H,q), 7.1–7.3(6H,m), 7.43(2H,br), 7.60(1H,d), 8.00(1H,s), 9.30(1H,br) | KBr; 3520, 3380, 3170, 2205, 1685, 1575 |
| 22 | CDCl$_3$/DMSO-d$_6$ = 1/1;3.87(3H,s), 3.93 (2H,s), 7.1–7.3(6H,m), 7.40(2H,br), 7.60(1H,d), 7.98(1H,s), 9.5(1H,br) | KBr; 3500, 3370, 3170, 2200, 1665, 1570 |
| 23 | CDCl$_3$/DMSO-d$_6$ = 1/1;3.92(2H,s), 7.06 (1H,d), 7.1–7.3(5H,m), 7.4(2H,br), 7.53(1H,d), 7.87(1H,s), 9.4(2H,br) | KBr; 3440, 3310, 3250, 2210, 1660, 1590, 1570 |
| 24 | CDCl$_3$/DMSO-d$_6$ = 1/1;3.90(2H,s), 7.1–7.8(12H,m), 8.38(1H,dd), 9.9(2H,br) | KBr; 3480, 3170, 1710, 1650, 1600, 1570 |
| 25 | CDCl$_3$/DMSO-d$_6$ = 1/1;4.75(2H,d), 7.3–7.7(18H,m), 8.8(1H,br), 9.84(1H,t) | KBr; 3570, 3200, 2850, 1690, 1635, 1610, 1570 |
| 26 | CDCl$_3$/DMSO-d$_6$ = 1/1;4.00(4H,s), 4.82 (2H,d), 7.1–7.3(18H,m), 9.0(1H,br), 9.78(1H,t) | KBr; 3300, 3200, 3010, 2880, 1660, 1610, 1590, 1570 |
| 27 | CDCl$_3$/DMSO-d$_6$ = 1/1;4.13(2H,s), 4.72 (2H,s), 6.37(2H,d), 6.90(2H,s), 7.2–7.5(6H,m), 7.57(1H,d), 9.8(3H,br) | KBr; 3550, 3180, 2800, 1660, 1620, 1580 |
| 28 | CDCl$_3$/DMSO-d$_6$ = 2/1;1.40(3H,t), 4.10(2H, q), 4.16(2H,s), 4.70(2H,d), 7.03–7.73 | |

TABLE 2-continued

| Compound No. | $^1$H-NMR spectrum δ (ppm) | IR spectrum (cm$^{-1}$) |
|---|---|---|
| | (15H,m), 9.10-9.60(1H,br), 9.7-10.0(1H,br) | |
| 29 | CDCl$_3$/DMSO-d$_6$ = 1/1;0.97(3H,t), 1.3-2.0(4H,m), 4.03(2H,t), 4.13(2H,s), 4.72(2H,s), 6.9-7.5(13H,m) | KBr; 3520, 3200, 3050, 2950, 2880, 1680, 1615, 1595 |
| 30 | CDCl$_3$/DMSO-d$_6$ = 1/1;1.02(3H,t), 1.3-1.9(4H,m), 4.03(2H,s), 4.08(2H,t), 4.59(2H,s), 6.88(2H,s), 7.1-7.7(11H, m), 8.0(1H,br) | KBr; 3520, 3200, 3020, 2900, 2870, 1670, 1590 |
| 31 | CDCl$_3$/DMSO-d$_6$ = 1/1;4.17(2H,s), 4.87 (2H,s), 5.17(2H,s), 6.9-7.6(16H,m), 9.8(2H,br) | KBr; 3500, 3200, 3060, 2770, 1680, 1630, 1610, 1590 |
| 32 | CDCl$_3$;1.30(12H,d), 3.12(2H,m), 7.10 (2H,d), 7.41(2H,s), 7.52(1H,br), 7.90 (1H,s), 10.21(1H,br) | |
| 33 | CDCl$_3$/DMSO-d$_6$ = 10/1;1.20(12H,d), 3.30 (2H,m), 4.70(2H,s), 7.13(2H,s), 7.30 (5H,m), 7.56(1H,s), 9.30-9.80(1H,br) | |
| 34 | CDCl$_3$/DMSO-d$_6$ = 10/1;1.23(12H,d), 2.96(2H,t), 3.40(2H,m), 3.80(2H,q), 7.20-7.40(7H,m), 7.53(1H,s), 8.40-8.70(1H,br), 9.46(1H,t) | |
| 35 | CDCl$_3$;1.23(12H,d), 3.36(2H,m), 4.76 (2H,d), 6.86-7.50(6H,m), 7.67(1H,s), 7.90-8.40(1H,br), 9.23-9.66(1H,br) | |
| 36 | CDCl$_3$/DMSO-d$_6$ = 10/1;1.26(12H,d), 3.36(2H,m), 4.70(2H,s), 7.20(2H,s), 7.33(4H,s), 7.07 (1H,s), 8.00-8.40(1H,br), 9.10-9.70(1H,br) | |
| 37 | CDCl$_3$/DMSO-d$_6$ = 10/1;1.23(12H,d), 3.33 (2H,m), 4.70(2H,d), 7.20-7.47(5H,m), 7.67 (1H,s), 7.80-8.20(1H,br), 9.20-9.60(1H,br) | |
| 38 | CDCl$_3$/DMSO-d$_6$ = 10/1;1.16(12H,d), 3.33 (2H,m), 3.73(3H,s), 4.70(1H,s), 6.80(2H, d), 7.16(2H,s), 7.30(2H,d), 7.60(1H,s), 7.85-8.20(1H,br), 9.00-9.60(1H,br) | |
| 39 | CDCl$_3$/DMSO-d$_6$ = 10/1;1.23(12H,d), 2.33(3H,s), 3.36(2H,m), 4.70(2H,d), 7.06-7.26(6H,m), 7.66(1H,s), 8.0-8.3(1H,br), 9.30(1H,t) | |
| 40 | CDCl$_3$/DMSO-d$_6$ = 10/1;1.23(12H,d), 3.36 (2H,m), 4.87(2H,d), 7.16(2H,s), 7.50 (1H,s), 7.60(2H,d), 8.20(2H,d), 8.2-8.6 (1H,br), 9.67(1H,br) | |
| 41 | CDCl$_3$/DMSO-d$_6$ = 10/1;1.23(12H,d), 3.16(2H,s), 3.33(2H,m), 4.80(2H,s), 6.96-7.90(7H,m), 8.0-8.4(1H,br), 9.63-9.76(1H,m) | |
| 42 | CDCl$_3$/DMSO-d$_6$ = 10/1;1.26(12H,d), 3.30 (2H,s), 3.36(2H,m), 4.66(2H,d), 6.63 (2H,d), 7.06(2H,d), 7.20(2H,s), 7.56 (1H,s), 8.4-8.8(1H,br), 9.5-9.7(1H,br) | |
| 43 | CDCl$_3$/DMSO-d$_6$ = 10/1;1.27(12H,d), 3.36 (2H,m), 4.80(2H,d), 6.36(2H,s), 7.26 (2H,s), 7.43(1H,s), 7.73(1H,s), 7.8-8.3 (1H,br), 9.1-9.5(1H,br) | |
| 44 | CDCl$_3$/DMSO-d$_6$ = 10/1;1.26(12H,d), 3.36 (2H,m), 4.96(2H,d), 6.9-7.3(5H,m), 7.73 (1H,s), 7.8-8.4(1H,br), 9.40(1H,t) | |
| 45 | CDCl$_3$;1.23(12H,d), 3.23(2H,m), 4.86 (2H,d), 7.06-7.46(5H,m), 7.66(1H,d), 7.76(1H,s), 8.50(1H,d), 8.7-9.1(1H,br) | |

The compound having the formula (I) of the present invention can be prepared by any processes as far as the compound can be obtained, and there are exemplified the following processes (a), (b) and (c) as the preparation processes.

(a) The compound having the formula (I) can be prepared by a condensation reaction of a benzaldehyde having the formula (II):

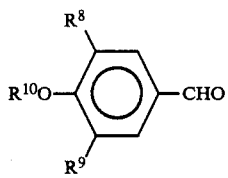

wherein $R^8$ and $R^9$ are the same or different and each is an alkyl group having 1 to 3 carbon atoms, phenyl group, benzyl group or phenethyl group, or $R^8$ is a group having the formula: $R^{11}O-$ in which $R^{11}$ is hydrogen atom, an alkyl group having 1 to 5 carbon atoms or benzyl group, and $R^9$ is benzyl group or a group:

PhSCH₂, and R¹⁰ is hydrogen atom, an alkyl group having 1 to 3 carbon atoms, an alkyl group substituted with ethers, e.g. methoxymethyl group or methoxyethoxymethyl group, benzyl group, an acyl group having the formula: COR¹² in which R¹² is hydrogen atom or an alkyl group having 1 to 3 carbon atoms, or a trialkylsilyl group such as trimethylsilyl group or tert-butyldimethylsilyl group; and a compound having the formula (III):

wherein R¹³ is cyano group and R¹⁴ is carbamoyl group, or R¹³ and R¹⁴ are taken together to represent a group: —CO—Y—CH₂CH₂— in which Y is oxygen atom or a group: —N(COR¹⁵)— in which R¹⁵ is hydrogen atom or an alkyl group having 1 to 3 carbon atoms, a group:

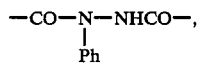

a group: —CONH—CS—S—, a group:

or a group:

or a compound having the formula (IV):

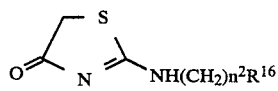 (IV)

wherein R¹⁶ is a group having the formula:

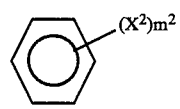

[in which X² is hydrogen atom, a halogen atom, methyl group, ethyl group, an alkoxyl group having the formula: R¹⁷O— (in which R¹⁷ is methyl group or ethyl group), nitro group, aminosulfonyl group or amino group, and m¹ is 1 or 2], pyridyl group, furyl group or thienyl group, and n² is 0 or an integer of 1 to 3; in the absence or presence of an acid or a base as a catalyst.

Examples of the acid used as the catalyst in the above-mentioned reaction are, for instance, a proton acid such as sulfuric acid, benzenesulfonic acid or p-toluenesulfonic acid, a Lewis acid such as boron trifluoride, and the like.

Examples of the base used as the catalyst are, for instance, ammonium or its salt, an organic base such as piperidine, pyrrolidine, monoethanolamine, pyridine, morpholine or 1,8-azabicyclo [5.4.0]undeca-7-ene or a salt thereof, an alkali metal salt of organic acid such as sodium acetate or potassium acetate, an alkali metal hydroxide such as sodium hydroxide or potassium hydroxide, an alkali metal amide such as lithium diisopropylamide, an alkali metal alcoholate such as sodium methylate or potassium butylate, an alkali metal hydride such as sodium hydride or potassium hydride, and the like.

When R¹⁰ in the starting material is remained in the obtained product as an alkyl, an alkyl group substituted with ethers, benzyl, an acyl or trialkylsilyl group due to noncatalytic reaction or the kind of catalyst employed, the desired compound can be obtained by eliminating R¹⁰. For eliminating R¹⁰, when R¹⁰ is an alkyl group or an alkyl group substituted with ethers, cleavage reaction which is carried out by using a Lewis acid such as aluminum chloride or boron tribromide, or a proton acid such as hydrogen bromide or trichloroacetic acid, other ether bond cleavage reaction, or the like can be adopted. When R¹⁰ is benzyl group, catalytic reduction reaction can be employed which is carried out by using a noble metal catalyst such as palladium carbon, as well as the above-mentioned ether bond cleavage reaction. When R¹⁰ is an acyl group, R¹⁰ can be eliminated by hydrolysis reaction which is carried out by using a base such as an alkali metal hydroxide such as sodium hydroxide or an alkaline earth metal hydroxide such as barium hydroxide. When R¹⁰ is trialkylsilyl group, R¹⁰ can be eliminated with water, methanol, an acid, fluorine ion, or the like.

When the reaction is carried out by employing an N-acyllactam and an acyl group is remained in the obtained product, the acyl group can be eliminated by hydrolysis reaction using a base such as alkali metal hydroxide such as sodium hydroxide to give the desired compound.

(b) The compound having the formula (I) can be prepared, according to O. Ister et al. [Helvetica Chimica Acta (Helv. Chim. Acta), 40, 1242(1957)], G. A. Howie et al. [Journal of Medicinal Chemistry (J. Med. Chem.), 17, 840(1974)], H. Wamhoff et al. [Synthesis, 331(1976)], and the like, by reacting a benzaldehyde having the formula (V):

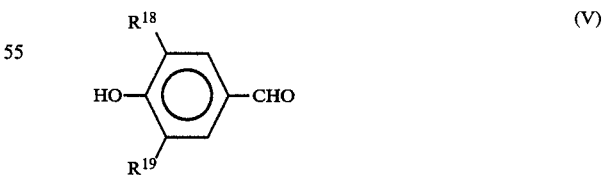

wherein R¹⁸ and R¹⁹ are the same or different and each is an alkyl group having 1 to 3 carbon atoms, phenyl group, benzyl group or phenethyl group, or R¹⁸ is a group: R²⁰O— in which R²⁰ is hydrogen atom, an alkyl group having 1 to carbon atoms or benzyl group, and R¹⁹ is benzyl group or the group: PhSCH₂; with an ylide having the formula (VI):

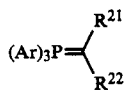 (VI)

wherein Ar is an aryl group, $R^{21}$ is a cyano group, and $R^{22}$ is carbamoyl group, or $R^{21}$ and $R^{22}$ are taken together to represent a group having the formula: $-CO-Z-CH_2CH_2-$ in which Z is oxygen atom or $-NH-$, a group having the formula:

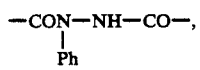

a group having the formula: $-CONH-CS-S-$, a group having the formula:

or a group having the formula:

or an ylide having the formula (VII):

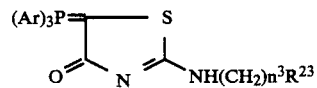 (VII)

wherein $R^{23}$ is a group having the formula:

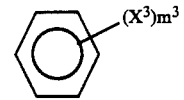

[in which $X^3$ is hydrogen atom, a halogen atom group, ethyl group, an alkoxyl group having the formula: $R^{24}O-$ (in which $R^{24}$ is methyl group or ethyl group), nitro group, aminosulfonyl group or amino group, and $m^3$ is 1 or 2], pyridyl group, furyl group or thienyl group, and $n^3$ is 0 or an integer of 1 to 3.

The above-mentioned reaction (b) is carried out according to the so-called Wittig reaction. For the ylide in the reaction (b), a ylide derived from a trialkyl phosphine such as tributyl phosphine or a arsine such as triphenyl arsine can also be used as well as the above-mentioned ylide (VI) or (VII).

(c) The compound, which is one of the embodiments of the present invention, having the formula (VIII):

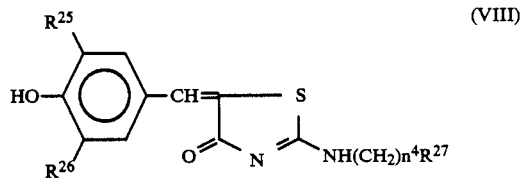 (VIII)

wherein $R^{25}$ and $R^{26}$ are the same or different and each is an alkyl group having 1 to 3 carbon atoms, phenyl group, benzyl group or phenethyl group, or $R^{25}$ is a group having the formula: $R^{28}O-$ in which $R^{28}$ is hydrogen atom, an alkyl group having 1 to 5 carbon atoms or benzyl group, $R^{26}$ is benzyl group or the group: $PhSCH_2$, $R^{27}$ is a group having the formula:

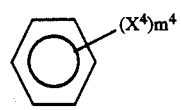

[in which $X^4$ is hydrogen atom, a halogen atom, methyl group, ethyl group, an alkoxyl group having the formula: $R^{29}O-$ (in which $R^{29}$ is methyl group or ethyl group), nitro group, aminosulfonyl group or amino group, and $m^4$ is 1 or 2], pyridyl group, furyl group or thienyl group, and $n^4$ is 0 or an integer of 1 to 3, can be prepared, according to M. T. Omar et al. [Acta Chimica Academiae Scientiorum Hungaricae (Acta Chim. Budapest)], 83, 359(1974); Indian Journal of Chemistry (Ind. J. Chem.) 20B, 849(1981)], by reacting a compound having the formula (IX):

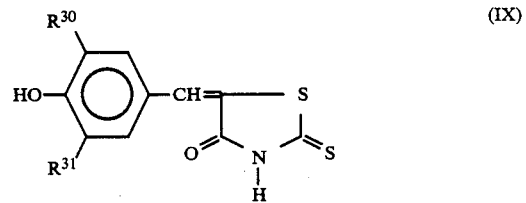 (IX)

wherein $R^{30}$ and $R^{31}$ are the same or different and each is an alkyl group having 1 to 3 carbon atoms, phenyl group, benzyl group or phenethyl group, or $R^{30}$ is a group having the formula: $R^{32}O-$ in which $R^{32}$ is hydrogen atom, an alkyl group having 1 to 5 carbon atoms or benzyl group, and $R^{31}$ is benzyl group or a group: $PhSCH_2$; or a compound having the formula (X):

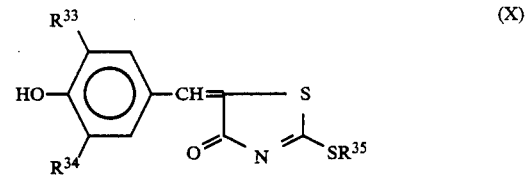 (X)

wherein $R^{33}$ and $R^{34}$ are the same or different and each is an alkyl group having 1 to 3 carbon atoms, phenyl group, benzyl group or phenethyl group, or $R^{33}$ is a group having the formula: $R^{36}O-$ in which $R^{36}$ is hydrogen atom, an alkyl group having 1 to 5 carbon atoms or benzyl group, $R^{34}$ is benzyl group or a group: $PhSCH_2$, and $R^{35}$ is an alkyl group having 1 to 3 carbon atoms; with an amine having the formula (XI):

$$H_2N(CH_2)_{n^5}R^{37} \qquad (XI)$$

wherein $R^{37}$ is a group having the formula:

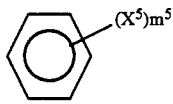

[in which $X^5$ is hydrogen atom, a halogen atom, methyl group, ethyl group, an alkoxyl group having the formula: $R^{38}O-$ (in which $R^{38}$ is methyl group or ethyl group), nitro group, aminosulfonyl group or amino group, and $m^5$ is 1 or 2], pyridyl group, furyl group or thienyl group, and $n^5$ is 0 or an integer of 1 to 3.

The novel hydroxystyrene derivative (I) of the present invention or a salt thereof is useful as an intermediate for preparing various organic compounds, and also useful as an antiallergic agent, 5-lipoxygenase inhibiting agent, an antibacterial agent, a tyrosine kinase inhibiting agent, an UV absorber or a reverse transcriptase inhibiting agent.

That is, the hydroxystyrene derivative can be expected to be used as an antiallergic agent and the like, by its antiallergic activity. By its 5-lipoxygenase inhibiting activity, it can be expected to be used as an antiasthmatic agent, an antiinflammatory agent, agents for the treatments of psoriasis, nephritis and myocardial infarction, an agent for preventing myocardial infarction and the like. By its antibacterial activity, it can be expected to be used as an antibacterial agent. By its tyrosine kinase inhibiting activity, it can be used as an antiasthmatic agent, an antiinflammatory agent, an anti-cancer agent, a carcinogenesis preventing agent, a metastasis-preventing agent, an agent used for the treatment of mental disease and the like. By its UV absorbing activity, it can be expected to be used for the prevention of erythema solare, used for preventing the deterioration of materials of organic high molecular weight compounds due to ultraviolet rays, and the like. Also, by its reverse transcriptase inhibiting activity, it can be expected to be used as an agent for preventing virus infections.

The above-mentioned activities of the compound of the present invention are specifically described by the following tests. In Tables 3 to 9, each compound No. corresponds to the compound No. in Tables 1 and 2.

The antiallergic activity of the compound of the invention is proved by the tests of inhibitory activity against passive cutaneous anaphylaxis (hereinafter referred to as "PCA") reaction, protecting effect against antigen-induced anaphylactic shock death and protecting effect against antigen-induced airway constriction.

(1) Inhibitory activity against homologous PCA reaction in rats

Antiserum was prepared according to I. Mota [Immunology, 7, 681(1964)] and the PCA reaction was conducted according to Maruyama et al. [Folia Pharmacologica Japonica, 74, 179(1978)].

PREPARATION OF ANTISERUM

An ovalbumin solution dissolved in physiological saline (2 mg/ml) was injected intramuscularly into both thighs of male Wistar rats weighing 200 to 260 g in a volume of 0.5 ml/100 g body weight, and pertussis vaccine (Bordetella pertussis, $2 \times 10^{10}$/ml, Chiba Serum Institute) was intraperitoneally administered at 1 ml/rat. Twelve days after sensitization, blood was taken from posterior aorta under ether anesthesia and serum was separated and stored at $-80°$ C.

PCA REACTION

In each group, 4 male Wistar rats weighing 180 to 210 g were used. Back of the rats was shaved and each 0.05 ml of antiserum diluted 32 times with physiological saline was injected intradermally at four sites on the back. After 48 hours, 1 ml of a mixture of ovalbumin (2 mg/ml) as an antigen and Evans blue (10 mg/ml) in the volume ratio of 1:1, which was dissolved in physiological saline was injected intravenously into the tail. Thirty minutes later, the rats were bled to death under ether anesthesia and the back skin of the rats was removed. The blue-dyed area formed by pigment exudation was measured and an inhibition rate (%) was calculated as compared with control according to the following equation.

$$\text{Inhibition rate (\%)} = \frac{A - B}{A} \times 100$$

A: Blue-dyed area in the control group
B: Blue-dyed area in the test compound group A test compound suspended in a 2.5% aqueous solution of gum arabic containing 0.2% Tween 80 was administered orally in a volume of 0.5 ml/100 g body weight 1 hour before the injection of antigen. To the control group, only the vehicle was administered. Tranilast which was a positive control compound was administered orally 30 minutes before the injection of antigen. The result shown in Table 3 proves that the compound of the present invention shows an excellent PCA reaction inhibitory activity.

TABLE 3

| Compound No. | Dose (mg/kg) | Inhibition rate (%) |
|---|---|---|
| 23 | 100 | 29 |
| 32 | 100 | 21 |
| 33 | 100 | 50 |
| 34 | 100 | 48 |
| 35 | 100 | 43 |
| 37 | 100 | 21 |
| 39 | 100 | 65 |
| 41 | 100 | 25 |
| tranilast | 300 | 40 |

(2) Protecting effect against antigen-induced anaphylactic shock death in actively sensitized guinea pigs Anaphylactic shock death caused by inhalation of antigen was observed according to John P. Devlin [Pulmonary and Antiallergic Drugs, John Wiley & Sons, 155(1985)] employing actively sensitized guinea pigs.

Each 100 mg/kg of body weight ovalbumin dissolved in physiological saline was injected into gluteus and into peritoneal cavity of male guinea pigs weighing 250 to 350 g. Three days later, the animals were further injected intraperitoneally with ovalbumin (100 mg/kg body weight) to conduct booster. Those animals were employed for testing 3 to 4 weeks after the sensitization.

In each group, 4 or more actively sensitized guinea pigs were pretreated by subcutaneously injecting pyrilamine (1 mg/kg body weight) 30 minutes before antigen inhalation to suppress histamine-dependent response and propranolol (1 mg/kg body weight) to enhance the response induced by other than histamine 10 minutes before the antigen inhalation.

The animal was placed in a desiccator with a capacity of about 5% and 0.5% aqueous solution of ovalbumin in the state of aerosol was inhaled with ultrasonic type nebulizer for five minutes. Anaphylactic shock death was observed and the animals survived for 90 minutes or more after antigen inhalation were estimated to be protected. All the animals of the control group died due to anaphylactic shock. The results are shown in Table 4. The compounds of the present invention and therapeutic antiasthmatic agent (tranilast, theophylline) were administered orally 30 minutes before the antigen inhalation. The result shown in Table 4 proves that the compounds of the present invention shows an excellent protecting effect against antigen-induced anaphylactic shock death.

TABLE 4

| Compound No. | Dose (mg/kg) | Protecting effect* |
|---|---|---|
| 35 | 10 | 2/4 |
| 36 | 100 | 1/4 |
| 37 | 100 | 1/4 |
| 38 | 100 | 1/4 |
| 39 | 100 | 1/4 |
| 41 | 10 | 1/4 |
| tranilast | 100 | 0/4 |
| theophylline | 30 | 2/4 |
| control | — | 0/20 |

(note) *Number of survivors/Number of animals used (3) Inhibitory activity against antigen-induced airwasy constriction in actively sensitized guinea pigs According to Orange and Moore [Journal of Immunology (J. Immunol.), 116, 392(1976)], an emulsion of a solution of ovalbumin dissolved in physiological saline (2 mg/ml) and Freund's complete adjuvant (Difco Laboratories), mixed in the equal volume was injected into peritoneal cavity of guinea pigs in the volume of 1 ml/guinea pig to sensitize them. Three or four weeks later, airway contraction caused by antigen-antibody reaction was measured in accordance with Konzett Rossler [Archiv für Experimental Pathologie und Pharmakologie (Arch. Exp. Path. Pharmak.), 195, 71(1940)]. That is, the sensitized guinea pigs (5 guinea pigs/group) were provided with artificial respiration by inserting a tracheal cannula under urethane anesthesia (1.5 g/kg body weight, intraperitoneal administration), and then, gallamine at 1 mg/kg body weight was injected intravenously to stop spontaneous respiration of the guinea pigs. Inhalation of 0.5% aqueous solution of ovalbumin was conducted using a nebulizer for 1 minute to increase antigen-induced airway constriction, at the same time, airway pressure was recorded through a transducer. Test compound was administered into jugular vein (i.v.) of the guinea pig 3 minutes before the antigen inhalation or administered orally (p.o.) 2 hours before the antigen inhalation. As a positive control compound, theophylline which was a drug for anti-asthma was used. The effect of the compound was estimated by calculating the maximum value of airway constriction (%) in comparison with the control group, according to the following equation. The result is shown in Table 5.

$$\text{Inhibition rate (\%)} = \frac{A - B}{A} \times 100$$

A: Maximum value of airway constriction in the control group

B: Maximum value of airway constriction in the test compound group

The result shown in Table 5 proves that the compounds of the present invention shows excellent inhibitory activity against antigen-induced airway constriction.

TABLE 5

| Compound No. | Route of administration | Dose (mg/kg) | Inhibition rate (%) |
|---|---|---|---|
| 7 | i.v. | 1 | 25 |
| 8 | i.v. | 1 | 43 |
| 9 | i.v. | 1 | 20 |
| 11 | i.v. | 1 | 52 |
| 11 | p.o. | 30 | 26 |
| 12 | i.v. | 1 | 32 |
| 26 | i.v. | 1 | 68 |
| 32 | i.v. | 2 | 23 |
| 33 | i.v. | 2 | 26 |
| 37 | i.v. | 1 | 21 |
| 39 | i.v. | 1 | 59 |
| 42 | i.v. | 5 | 33 |
| 43 | i.v. | 5 | 21 |
| 45 | i.v. | 1 | 42 |
| theophylline | i.v. | 1 | 31 |

5-Lipoxygenase inhibiting activity of the compound of the present invention was measured referring to the method for measuring 5-lipoxygenase activity by K. Ochi et al. [Journal of Biological Chemistry (J. Biol. Chem.), 258, 5754(1983)].

Sterilized 2% solution of casein (pH 7) was injected intraperitoneally into Hartley guinea pigs in a volume of 5 ml/100 g body weight. Fifteen hours later, the guinea pigs were killed and peritoneal exudate cells thereof were collected. After the exudate cells were washed with 17 mM Tris-HCl buffer (pH 7.4) containing 0.74% ammonium chloride to remove contaminating erythrocytes in the exudate cells suspension, the cells were washed with buffer A (130 mM NaCl, 1 mM EDTA, 25 mM sodium phosphate, pH 7.4). The washed cells were suspended in buffer B (50 mM sodium phosphate, 1 mM EDTA, 0.1% gelatin, pH 7.4) at $10^8$ cells/ml, sonicated and centrifuged at 10,000×g for 20 minutes under the cold atmosphere. The obtained supernatant was further centrifuged at 105,000×g for 60 minutes under the cold atmosphere. The cytosol fraction was used as an enzyme solution.

The enzyme solution was preincubated with the test compound in the presence of 1 mM $CaCl_2$, 1 mM reduced glutathione (GSH) and 2 mM ATP at 30° C. for 5 minutes in 0.2 ml of a reaction mixture and the mixture was further incubated at 30° C. for 5 minutes by adding 20 μM [1-$^{14}$C] arachidonic acid (0.1 μCi) thereto. The test compounds were dissolved in ethanol to give the reaction mixture containing 2% ethanol as a final concentration. Only ethanol was added to the reaction mixture as a control group.

To the reaction mixture were added 2.5 ml of a mixture of chloroform and methanol (2/1 by volume) and 0.3 ml of 40 mM citric acid to stop the reaction. The mixture was vortexed and an organic solvent layer was evaporated to dryness under nitrogen gas. After dissolving the dried organic layer in a fixed amount of the mixture of chloroform and methanol (2/1 by volume), it was spotted on a silica gel plate (Kiesel gel 60F254, E. Merck) and products were separated using a developer (the organic solvent layer of ethyl acetate/water/2,2,4- trimethylpentane/acetic acid=11/10/5/2 by volume). After the radioactive position of the product was determined by means of a radioautography, an area equivalent to that of 5-hydroxyeicosatetraenoic acid (hereinafter referred to as "5-HETE") was scraped off, and then its radioactivity was measured with a liquid scintillation counter. With regarding the amount of the generated 5-HETE as the 5-lipoxygenase inhibiting activity, the inhibition rate (%) in comparison with the control group was calculated according to the following equation.

$$\text{Inhibition rate } (\%) = \frac{A - B}{A} \times 100$$

A: Value of radioactivity in the control group
B: Value of radioactivity in the test compound group The 5-lipoxygenase inhibiting activity of the compounds of the present invention is shown in Table 6. The result shown in Table 6 proves that the compounds of the present invention sufficiently inhibits 5-lipoxygenase activity.

TABLE 6

| Compound No. | Concentration* ($\mu$M) | Inhibition rate (%) |
|---|---|---|
| 2 | 10 | 78 |
| 4 | 10 | 85 |
| 7 | 1 | 88 |
| 8 | 1 | 61 |
| 9 | 1 | 91 |
| 10 | 1 | 23 |
| 11 | 1 | 87 |
| 12 | 1 | 84 |
| 13 | 1 | 86 |
| 14 | 1 | 27 |
| 16 | 10 | 28 |
| 20 | 10 | 83 |
| 22 | 10 | 63 |
| 23 | 10 | 85 |
| 24 | 1 | 48 |
| 25 | 1 | 23 |
| 26 | 1 | 84 |
| 29 | 1 | 86 |
| 30 | 1 | 87 |
| 31 | 1 | 49 |
| 33 | 10 | 82 |
| 35 | 10 | 89 |
| 36 | 10 | 84 |
| 37 | 10 | 89 |
| 38 | 10 | 88 |
| 39 | 10 | 87 |
| 40 | 10 | 87 |
| 41 | 10 | 89 |
| 42 | 10 | 88 |
| 43 | 1 | 53 |
| 45 | 1 | 36 |

(note) *Concentration of the test compound in the reaction mixture

The antibacterial activity against Gram-positive bacteria of the compound of the present invention was measured according to a standard method of Nippon Kagaku Ryoho Gakkai [Nippon Kagaku Ryoho Gakkaishi (Journal of the Chemical therapy of Japan), 29, 76(1981)].

As for gram-positive bacteria, after cultivation in Mueller Hinton broth medium (made by Difco Co., Ltd.), there was prepared a bacterial suspension for inoculation containing about $10^6$ of the bacteria per 1 ml of the Mueller Hinton broth medium. On the other hand, the test compound was added to Mueller Hinton agar medium (made by Difco Co., Ltd.) so as to give agar plate medium containing test samples which are twofold serial diluted. Then, the above-mentioned bacterial suspension for inoculation was streaked to each agar medium for about 2 cm with a looped nichrome wire (inner diameter: about 1 mm).

After that the each agar plate medium was cultured at 37° C. for 18 to 20 hours, the growth of the test bacteria was determined. The minimum concentration of the test compound, which completely inhibited the growth of the test bacteria, was decided as a minimal inhibitory concentration (hereinafter referred to as "MIC").

As for acid-fast bacteria, after cultured in glycerol broth medium, there was prepared a bacterial suspension for inoculation containing about $10^6$ of the bacteria per 1 ml of the medium. On the other hand, there were prepared some glycerol Czapek agar plating media with adding the test compounds, and thereto the bacterial suspension for inoculation was streaked.

After the each agar plating medium, to which the acid-fast bacteria was streaked, was cultured at 37° C. for 40 to 42 hours, MIC was determined as defined above.

As the result, each MIC of the compounds (1), (2), (4), (11), (15), (16), (19) and (20) against *Micrococcus luteus* IFO 13867 was not more than 6 $\mu$g/ml, not more than 6 $\mu$g/ml, not more than 6 $\mu$g/ml, 12 $\mu$g/ml, 60 $\mu$g/ml, not more than 15 $\mu$g/ml, 50 $\mu$g/ml and not more than 50 $\mu$g/ml respectively; each MIC of the compounds (1), (2), (11), (15), (16), (19), (20) and (41) against *Bacillus subtilis* IFO 3134 was not more than 6 $\mu$g/ml, not more than 6 $\mu$g/ml, not more than 6 $\mu$g/ml, 100 $\mu$g/ml, not more than 15 $\mu$g/ml, 100 $\mu$g/ml, 50 $\mu$g/ml and 25 $\mu$g/ml respectively; each MIC of the compounds (1), (2), (11), (15), (16), (19), (20) and (41) against *Staphylococcus aureus* IFO 12732 was 12 $\mu$g/ml, 12 $\mu$g/ml, 25 $\mu$g/ml, 60 $\mu$g/ml, not more than 15 $\mu$g/ml, 100 $\mu$g/ml, 100 $\mu$g/ml and 50 $\mu$g/ml respectively; and each MIC of the compounds (1), (15), (16), (19), (28), (30), (31), (32), (33), (34), (35), (41), (42), (43), (44) and (45) against *Mycobacterium smegmatis* ATCC 607 was 6 $\mu$g/ml, not more than 15 $\mu$g/ml, not more than 15 $\mu$g/ml, not more than 6 $\mu$g/ml, not more than 15 $\mu$g/ml, not more than 6 $\mu$g/ml, not more than 6 $\mu$g/ml, not more than 6 $\mu$g/ml, not more than 15 $\mu$g/ml, not more than 6 $\mu$g/ml, 15 $\mu$g/ml, 25 $\mu$g/ml, not more than 15 $\mu$g/ml, not more than 6 $\mu$g/ml, 2 $\mu$g/ml and not more than 6 $\mu$g/ml respectively.

Consequently, it was found that the compounds of the present invention were effective on both gram-positive and acid-fast bacteria.

Tyrosine kinase inhibiting activity of the compound of the present invention was measured referring to a method for measuring tyrosine kinase activity by G. Carpenter or by S. Cohen et al. [J. Biol. Chem., 254, 4884(1979); J. Biol. Chem., 257, 1528(1982)].

Cell line A-431 derived from human carcinoma (ATCC CRL1555) was cultured at 37° C. under the condition of 5% $CO_2$ in Dulbecco's modified Eagle's medium (made by NISSUI PHARMACEUTICAL CO., LTD.) containing 10% by volume fetal bovine serum, 50 $\mu$g/ml of streptomycin, 50 IU/ml of penicillin G and 50 $\mu$g/ml of kanamycin. The obtained cells were treated according to the above-mentioned method of Cohen or Carpenter et al. to give membrane preparation containing epidermal growth factor receptor-tyrosine kinase complex (hereinafter referred to as "membrane preparation"). The membrane preparation was employed in the following measurement without solubilization.

A test compound dissolved in dimethylsulfoxide (hereinafter referred to as "DMSO") was added to a mixture of 20 mM of N-2-hydroxyethylpiperazine-N'-2-ethanesulfonic acid buffer (pH 7.4), 1 mM of MnCl$_2$, 7.5 µg of bovine serum albumin and the membrane preparation (10 µg as protein). After incubation at 0° C. for 5 minutes, 100 ng of epidermal growth factor (hereinafter referred to as "EGF") was added thereto and the mixture was further incubated at 0° C. for 15 minutes. [γ-$^{32}$P]ATP (3000 Ci/mmol, 0.1 µCi) was added thereto to make final volume of 70 µl. After incubation at 0° C. for 15 minutes, 50 µl of the reaction mixture was soaked into Whatman 3 MM filter paper (made by Whatman Ltd.) and immediately the reaction was stopped by an aqueous solution of 10% by weight trichloroacetic acid containing 10 mM sodium pyrophosphate. The filter paper was sufficiently washed with the same solution and then washed with ethanol, and dried. Radioactivity present in the filter paper was measured by liquid scintillation counter (A). Also, radioactivity was measured in case of the reaction without EGF (B), the reaction without the test compound (C), and the reaction without both EGF and the test compound (D) as a control.

Tyrosine kinase inhibition rate (%) was calculated by the following equation.

$$\text{Inhibition rate (\%)} = \frac{(C - D) - (A - B)}{C - D} \times 100$$

The result proves that the compounds of the present invention shows excellent tyrosine kinase inhibitory activity.

There is shown each tyrosine kinase inhibition rate of the compounds of the present invention in Table 7.

TABLE 7

| Compound No. | Concentration* (µM) | Inhibition rate (%) |
|---|---|---|
| 1 | 1 | 23 |
| 2 | 1 | 20 |
| 3 | 1 | 45 |
| 4 | 1 | 74 |
| 5 | 1 | 42 |
| 7 | 10 | 59 |
| 8 | 10 | 69 |
| 9 | 10 | 50 |
| 10 | 1 | 40 |
| 11 | 10 | 52 |
| 12 | 10 | 30 |
| 14 | 1 | 43 |
| 15 | 1 | 100 |
| 16 | 1 | 100 |
| 17 | 1 | 25 |
| 18 | 1 | 87 |
| 19 | 1 | 74 |
| 20 | 1 | 46 |
| 21 | 1 | 98 |
| 22 | 1 | 84 |
| 23 | 10 | 60 |
| 24 | 1 | 37 |
| 25 | 10 | 72 |
| 26 | 10 | 62 |
| 27 | 1 | 58 |
| 28 | 1 | 66 |
| 29 | 1 | 63 |
| 30 | 1 | 70 |
| 31 | 10 | 41 |
| 32 | 1 | 74 |
| 33 | 10 | 69 |
| 34 | 1 | 63 |
| 35 | 1 | 70 |
| 36 | 10 | 59 |
| 37 | 10 | 83 |
| 38 | 10 | 85 |
| 39 | 10 | 43 |

TABLE 7-continued

| Compound No. | Concentration* (µM) | Inhibition rate (%) |
|---|---|---|
| 40 | 10 | 21 |
| 41 | 10 | 70 |
| 42 | 1 | 85 |
| 43 | 10 | 95 |
| 44 | 1 | 80 |
| 45 | 10 | 90 |

(note) *Concentration of the test compound in the reaction mixture

Additionally, the compounds of the present invention have UV absorbing activity and thus there are expected to use the compounds as the UV absorber in order to prevent a living body from erythema solare (generally called as sunburn), prevent organic high molecular materials (e.g. plastics, gum, paints and the like) from declining by UV-ray or prevent photographs and pictures from discoloring by UV-ray.

Each UV absorption spectrum of the compounds of the present invention was measured according to the conventional method, in which methanol was used as a solvent, and thereby molar extinction coefficient thereof was calculated. The results were shown in Table 8. It is found that, as shown in Table 8, the compounds of the present invention rather strongly absorb UV-ray.

TABLE 8

| Compound No. | λ max (nm) | molar extinction coefficient |
|---|---|---|
| 4 | 257 | $1.87 \times 10^4$ |
|   | 361 | $1.80 \times 10^4$ |
| 15 | 271 | $2.04 \times 10^4$ |
|   | 348 | $2.11 \times 10^4$ |
| 16 | 249 | $1.51 \times 10^4$ |
|   | 347 | $2.40 \times 10^4$ |
| 18 | 304 | $1.87 \times 10^4$ |

There was found the following point by using reverse transcriptase derived from Moloney-Murine Leukemia Virus (hereinafter referred to as "M-MLV").

The compound of the present invention was dissolved in DMSO to give a 100 mM solution thereof. Then, the solution was diluted with distilled water containing DMSO to give a solution of the test compound having a defined concentration. A mixed ratio of DMSO and distilled water was adjusted so that the concentration of DMSO at this time is 10% by volume and a final concentration of DMSO at the beginning of a reaction is 1% by volume.

The thus prepared solution of the test compound was mixed with a solution containing 50 mM of Tris-HCl buffer (pH 8.3), 8 mM of MgCl$_2$, 30 mM of NaCl, 50 mM of dithiothreitol (made by Wako Pure Chemical Industries Ltd.), 0.2 mM of thymidine-5'-triphosphate (made by Pharmacia K. K.) and 6 U/ml of reverse transcriptase derived from M-MLV (made by Pharmacia K. K.), and preincubated at 37° C. for 30 minutes. After there was added thereto 10 µg/ml of polyadenylic acid (made by PL Biochemicals Co., Ltd.), 0.01 U/ml of oligodeoxy thymidylic acid (made by Pharmacia K. K.) and 10 µCi/ml of [methyl-$^3$H] thymidine-5'-triphosphate (made by Amersham Japan Co., Ltd., 47 Ci/mmol) to give a reaction mixture, the mixture was further incubated at 37° C. for 30 minutes, followed by cooling with ice to stop the reaction.

The radioactivity incorporated into deoxyribonucleic acids was measured according to the method of Linteril et al (Science, 170, 447 to 449 (1967)). A defined volume of the reaction mixture was soaked into DE-81 filter paper (made by Whatman Ltd.), the filter paper was washed with 5% by weight of $Na_2HPO_4$ solution for three times, and with distilled water and ethanol successively, and then dried. Radioactivity contained in the filter paper was measured by liquid scintillation counter to give the each radioactivity of the test solution groups.

On the other hand, the same procedure as above was carried out using DMSO-distilled water without the test compound instead of using the test solution, to give the value of radioactivity of a control group.

Reverse transcriptase derived from M-MLV inhibition rate (%) was calculated by the following equation.

$$\text{Inhibition rate (\%)} = \frac{A - B}{A} \times 100$$

The typical examples of reverse transcriptase derived from M-MLV inhibiting activity of the compounds of the present invention are shown in Table 9.

The results proves that the compounds shown in Table 1 have strong inhibiting activity against reverse transcriptase derived from M-MLV and thus it can be expected that the compounds show sufficient growth inhibiting effect on retrovirus having reverse transcriptase.

TABLE 9

| Compound No. | Concentration* (μM) | Inhibition rate (%) |
|---|---|---|
| 1 | 1 | 96 |
| 2 | 1 | 95 |
| 5 | 10 | 87 |
| 6 | 10 | 98 |
| 7 | 1 | 98 |
| 8 | 1 | 98 |
| 9 | 1 | 73 |
| 10 | 10 | 61 |
| 11 | 1 | 94 |
| 15 | 10 | 59 |
| 19 | 1 | 75 |
| 20 | 10 | 97 |
| 24 | 1 | 91 |
| 26 | 10 | 76 |
| 27 | 1 | 73 |
| 31 | 10 | 61 |
| 42 | 10 | 50 |

(Note) *Concentration of the test compound in the reaction mixture (Acute toxicity test)

In each group, 6 female ICR mice weighing 23 to 26 g were employed. The compounds (1) to (45) suspended in an aqueous solution of 2.5% gum arabic containing 0.2% Tween 80 were administered orally to each mouse in a volume of 0.1 ml/10 g body weight. The general symptoms of the mice were observed for two weeks after the administration. The $LD_{50}$ (mg/kg) values were estimated from the ratio of the number of dead mice to the number of mice used. As a result, there were observed no dead mice at a dose of 500 mg/kg. The $LD_{50}$ of the compounds (1) to (45) of the present invention was estimated to be not less than 500 mg/kg, which proved a low toxicity of the compounds of the present invention.

(Preparations and Dosage)

The antiallergic agents, 5-lipoxygenase inhibiting agents, antibacterial agents, tyrosine kinase inhibiting agents, UV absorber or reverse transcriptase inhibiting agents of the present invention can be administered orally, rectally, or parenterally in pharmaceutical dosage form, for example, tablets, capsules, fine subtilaes, syrups, suppositories, ointments, injections, and the like.

As for excipients in the formulations of the antiallergic agents, 5-lipoxygenase inhibiting agents, antibacterial agents, tyrosine kinase inhibiting agents, UV absorber or reverse transcriptase inhibiting agents of the present invention, organic or inorganic pharmaceutically acceptable excipient material is employed in a solid or liquid state, which is usually inactive and suited for oral, rectal or parenteral administration. Examples of such excipient are, for instance, crystalline cellulose, gelatin, lactose, starch, magnesium stearate, talc, vegetable or animal fat and oil, gum, polyalkyleneglycol, and the like. The ratio of the compound of the present invention having the formula (I), contained in the antiallergic agents, 5-lipoxygenase inhibiting agents, antibacterial agents, tyrosine kinase inhibiting agents, UV absorber or reverse transcriptase inhibiting agents as an active ingredient in the formulation any vary in the range from 0.2 to 100%.

The antiallergic agents, 5-lipoxygenase inhibiting agents, antibacterial agents, the tyrosine kinase inhibiting agents, UV absorber or reverse transcriptase inhibiting agents of the present invention may contain other antiallergic agents, 5-lipoxygenase inhibiting agents, antibacterial agents, tyrosine kinase inhibiting agents, UV absorber, reverse transcriptase inhibiting agents or any other drugs, which are compatible with the agents of the present invention. In this case, it is needless to say that the antiallergic agents, 5-lipoxygenase inhibiting agents, antibacterial agents, tyrosine kinase inhibiting agents, UV absorber or reverse transcriptase inhibiting agents of the present invention may not be the principal ingredients in the formulation.

The antiallergic agents, 5-lipoxygenase inhibiting agents, antibacterial agent, the tyrosine kinase inhibiting agents, UV absorber or reverse transcriptase inhibiting agents of the present invention are administered at a dose where the desired activity is generally achieved without any side effects.

Though a practical dose should be determined by a physician, the compound of the present invention having the formula (I), which is an active ingredient of the agents of the present invention, is generally administered at a dose from 10 mg to 10 g, preferably from about 20 mg to 5 g, for an adult a day. The antiallergic agents, 5-lipoxygenase inhibiting agents, antibacterial agents, tyrosine kinase inhibiting agents, UV absorber or reverse transcriptase inhibiting agents of the present invention can be administered as a pharmaceutical formulation which contains 1 mg to 5 g, preferably 3 mg to 1 g of the compound having the formula (I) as an active ingredient.

The present invention is more specifically described and explained by means of the following Examples. It is to be understood that the present invention is not limited to Examples.

EXAMPLE 1

Preparation of the compound (1)

In 100 ml of benzene were dissolved 1.37 g of 3,5-diphenyl-4-hydroxybenzaldehyde and 0.82 g of rhodanine, and thereto 0.1 ml of piperidine and 0.5 ml of acetic acid were added. The mixture was heated under reflux for 5 hours in Dean-Stark apparatus while removing water produced. After cooling, the deposited crystals were filtered and subjected to crystallization from a mixed solvent of benzene and acetone to give 1.2 g (yield: 62%) of the compound (1).

The melting point and data of elementary analysis of the obtained compound (1) are shown in Table 1. And results of $^1$H-NMR and IR of the obtained compound (1) are shown in Table 2.

EXAMPLE 2

Preparation of the compound (4)

In 70 ml of benzene were dissolved 1.51 g of 3,5-dibenzyl-4-hydroxybenzaldehyde and 0.67 g of oxyindol, and thereto 0.1 ml of piperidine and 0.5 ml of acetic acid were added. The mixture was heated under reflux for 5 hours in Dean-Stark apparatus while removing water produced. After cooling, the solvent was distilled away under reduced pressure. The obtained residue was dissolved in 200 ml of chloroform, washed with water and dried with sodium sulfate. Chloroform was distilled away under reduced pressure, the residue was subjected to crystallization from ethanol to give 600 mg (yield: 29%) of the compound (4).

The melting point and data of elementary analysis of the obtained compound (4) are shown in Table 1. And results of $^1$H-NMR and IR of the obtained compound (4) are shown in Table 2.

EXAMPLE 3

Preparation of the compound (5)

In 70 ml of benzene were dissolved 0.61 g of 3,5-dibenzyl-4-hydroxybenzaldehyde and 0.39 g of 2H-1,4-benzothiazine-3(4H)-one-1,1-dioxide, and thereto 0.1 ml of piperidine and 0.5 ml of acetic acid were added. The mixture was heated under reflux for 5 hours in Dean-Stark apparatus while removing water produced. After cooling, the solvent was distilled away under reduced pressure. The obtained residue was subjected to a column-chromatography (carrier: silica-gel) and eluted with mixed solvent of chloroform/methanol (98/2: v/v). A fraction containing the desired compound was concentrated and the obtained residue was subjected to crystallization from benzene to give 180 mg (yield: 19%) of the compound (5).

The melting point and data of elementary analysis of the obtained compound (5) are shown in Table 1. And results of $^1$H-NMR and IR of the obtained compound (5) are shown in Table 2.

EXAMPLE 4

Preparation of the compound (7)

To 100 ml of benzene were added 2.6 g of 5-phenylthiomethylprotocatechuic aldehyde, 1.33 g of rhodanine, 0.1 ml of piperidine and 0.5 ml of acetic acid. The mixture was heated under reflux for 5 hours in Dean-Stark apparatus while removing water produced. After cooling, the deposited crystals were filtered off from the reaction mixture and the obtained crystals were recrystallized from ethanol to give 2.78 g (yield: 74%) of the compound (7).

The melting point and data of elementary analysis of the obtained compound (7) are shown in Table 1. And results of $^1$H-NMR and IR of the obtained compound (7) are shown in Table 2.

EXAMPLE 5

Preparation of the compound (11)

In 70 ml of benzene were dissolved 0.78 g of 5-phenylthiomethylprotocatechuic aldehyde and 0.4 g of oxyindol, and thereto 0.1 ml of piperidine and 0.5 ml of acetic acid were added. The mixture was heated under reflux for 5 hours in Dean-Stark apparatus while removing water produced. After cooling, the deposited crystals were filtered off from the reaction mixture and washed with benzene. And the obtained crystals were recrystallized from a mixed solvent of benzene and acetone to give 1.0 g (yield: 90%) of the compound (11).

The melting point and data of elementary analysis of the obtained compound (11) are shown in Table 1. And results of $^1$H-NMR and IR of the obtained compound (11) are shown in Table 2.

EXAMPLE 6

Preparation of the compound (12)

A condensation of 0.7 g of 3-benzyloxy-4-hydroxy-5-phenylthiomethylbenzaldehyde and 0.27 g of oxyindol was carried out in the same manner as in the above Example 1. And the obtained residue was subjected to a column-chromatography (carrier: silica-gel) and eluted with mixed solvent of chloroform/methanol (98/2: v/v). After a fraction containing the desired compound was concentrated under reduced pressure, the fraction was subjected to crystallization from ethanol to give 0.62 g (yield: 66%) of the compound (12).

The melting point and data of elementary analysis of the obtained compound (12) are shown in Table 1. And results of $^1$H-NMR and IR of the obtained compound (12) are shown in Table 2.

EXAMPLE 7

Preparation of the compound (15)

In 200 ml of benzene were dissolved 2.90 g of 3,5-diphenyl-4-hydroxybenzaldehyde and 840 mg of α-cyanoacetamide, and thereto 0.1 ml of piperidine and 0.5 ml of acetic acid were added. The mixture was heated under reflux for 5 hours in Dean-Stark apparatus while removing water produced. After the solvent was distilled away under reduced pressure, the obtained residue was subjected to a column-chromatography (carrier: silica-gel) and eluted with a mixed solvent of chloroform/methanol (98/2: v/v). A fraction containing the desired compound was concentrated and the obtained residue was subjected to crystallization from a mixed solvent of benzene and acetone to give 11.15 g (yield: 32 of the compound (15).

The melting point and data of elementary analysis of the obtained compound (15) are shown in Table 1. And results of $^1$H-NMR and IR of the obtained compound (15) are shown in Table 2.

EXAMPLE 8

Preparation of the compound (17)

To 50 ml of acetonitrile were added 760 mg of 3,5-dibenzyl-4-hydroxybenzaldehyde and 1.04 g of α-triphenylphosphoranylidene-γ-butyrolactone. The mixture was heated and stirred overnight at 80° C. After cooling, the deposited crystals were filtered and subjected to crystallization from ethanol to give 450 mg (yield: 48%) of the compound (17).

The melting point and data of elementary analysis of the obtained compound (17) are shown in Table 1. And results of $^1$H-NMR and IR of the obtained compound (17) are shown in Table 2.

EXAMPLE 9

Preparation of the compound (18)

In 50 ml of dried benzene was suspended 0.6 g of sodium hydride under nitrogen atmosphere, to which a solution of 1.73 g of 3,5-dibenzyl-4-methoxymethoxybenzaldehyde and 1.27 g of N-acetylpyrrolidone dissolved in 20 ml of benzene was added dropwise, subsequently heated and stirred overnight at 50° C. After cooling, the reaction solution was added to an ice water and extracted with chloroform. The solvent was distilled away from the obtained extract under reduced pressure. The obtained residue was dissolved in 50 ml of dried methylene chloride, which was added with 4 ml of trifluoroacetic acid and stirred for 3 hours at room temperature. The solvent was distilled away from the solution under reduced pressure, the obtained residue was subjected to a column-chromatography (carrier: silica-gel) and eluted with mixed solvent of chloroform/methanol (98/2: v/v). A fraction containing the desired compound was concentrated and the obtained residue was subjected to crystallization from ethanol to give 450 mg (yield: 21%) of the compound (18).

The melting point and date of elementary analysis of the obtained compound (18) are shown in Table 1. And results of $^1$H-NMR and IR of the obtained compound (18) are shown in Table 2.

EXAMPLE 10

Preparation of the compound (19)

In 100 ml of benzene were dissolved 1.37 g of 3,5-diphenyl-4-hydroxybenzaldehyde and 0.88 g of 1-phenyl-3,5-pyrazolidinedion, and thereto 0.1 ml of piperidine and 0.5 ml of acetic acid were added. The mixture was heated under reflux for 5 hours in Dean-Stark apparatus while removing water produced. After cooling, the deposited crystals were filtered and subjected to crystallization from ethanol to give 600 mg (yield: 28%) of the compound (19).

The melting point and data of elementary analysis of the obtained compound (19) are shown in Table 1. And results of $^1$H-NMR and IR of the obtained compound (19) are shown in Table 2.

EXAMPLE 11

Preparation of the compound (25)

To 100 ml of benzene were added 1.37 g of 3,5-diphenyl-4-hydroxybenzaldehyde, 0.82 g of rhodanine, 0.1 ml of piperidine and 0.5 ml of acetic acid. The mixture was heated under reflux for 5 hours in Dean-Stark apparatus while removing water produced. The deposited crystals was filtered off from the reaction mixture. After drying, the deposited crystals were heated under reflux for 5 hours with 1.1 ml of benzylamine in 50 ml of ethanol. After cooling, the solvent was distilled away under reduced pressure. The residue was subjected to a column-chromatography (carrier: silica-gel) and eluted with mixed solvent of chloroform/methanol (100/2: v/v). After a fraction containing the desired compound was concentrated under reduced pressure, the fraction was subjected to crystallization from ethanol to give 0.60 g (yield: 26%) of the compound (25).

The melting point and data of elementary analysis of the obtained compound (25) are shown in Table 1. And results of $^1$H-NMR and IR of the obtained compound (25) are shown in Table 2.

EXAMPLE 12

Preparation of the compound (26)

To 100 ml of benzene were added 3.02 g of 3,5-dibenzyl-4-hydroxybenzaldehyde, 1.33 g of rhodanine, 0.1 ml of piperidine and 0.5 ml of acetic acid. The mixture was heated under reflux for 5 hours in Dean-Stark apparatus while removing water produced. The deposited crystals were filtered off from the reaction mixture. After drying, the deposited crystals were heated under reflux for 5 hours with 2.2 ml of benzylamine in 100 ml of ethanol. After cooling, the solvent was distilled away under reduced pressure. The obtained residue was subjected to a column-chromatography (carrier: silica-gel) and eluted with mixed solvent of chloroform/methanol (100/2: v/v). After a fraction containing the desired compound was concentrated under reduced pressure, the fraction was subjected to crystallization from ethanol to give 2.0 g (yield: 41%) of the compound (26).

The melting point and data of elementary analysis of the obtained compound (26) are shown in Table 1. And results of $^1$H-NMR and IR of the obtained compound (26) are shown in Table 2.

EXAMPLE 13

Preparation of the compound (28)

To 100 ml of ethanol were added 4.04 g of 5-(3-ethoxy-4-hydroxy-5-phenylthiomethylbenzylidene)-rhodanine obtained by the condensation reaction of 5-phenylthiomethylethylvanillin and rhodanine in the same manner as above and 2.2 ml of benzylamine. The mixture was heated under reflux for 5 hours. After cooling, the solvent was distilled away under reduced pressure. The obtained residue was subjected to a column-chromatography (carrier: silica-gel) and eluted with chloroform. After a fraction containing the desired compound was concentrated under reduced pressure, the fraction was subjected to crystallization from ethanol to give 1.96 g (yield: 38%) of the compound (28).

The melting point and data of elementary analysis of the obtained compound (28) are shown in Table 1. And results of $^1$H-NMR and IR of the obtained compound (28) are shown in Table 2.

EXAMPLE 14

Preparation of the compound (30)

To 50 ml of ethanol were added 0.80 g of 5-(3-n-butyloxy-4-hydroxy-5-benzylbenzylidene)-rhodanine obtained by the condensation reaction of 3-n-butyloxy-4-hydroxy-5-benzylbenzaldehyde and rhodanine in the same manner as above and 0.44 ml of benzylamine. The mixture was heated under reflux for 5 hours. After cooling, the solvent was distilled away under reduced pressure. The obtained residue was subjected to a column-chromatography (carrier: silica-gel) and eluted with a mixed solvent of chloroform/methanol (10/1: v/v). After a fraction containing the desired compound was concentrated under reduced pressure, the fraction was subjected to crystallization from ethanol to give 0.72 g (yield: 76%) of the compound (30).

The melting point and data of elementary analysis of the obtained compound (30) are shown in Table 1. And

EXAMPLE 15

Preparation of the compound (33)

In 30 ml of ethanol was dissolved 966 mg of 5-(3,5-diisopropyl-4-hydroxybenzylidene)-rhodanine, and thereto 624 mg of benzylamine was added. The mixture was heated under reflux for 5 hours. Ethanol was distilled away under reduced pressure, and the obtained residue was dissolved in chloroform. After washing with water, the solution was concentrated to dryness. The obtained concentrate was subjected to a column-chromatography (carrier: silica-gel) and eluted with chloroform. A fraction containing the desired compound was collected, concentrated and dried to give 660 mg (yield: 56%) of the compound (33).

The melting point and data of elementary analysis of the obtained compound (33) are shown in Table 1. And results of $^1$H-NMR and IR of the obtained compound (33) are shown in Table 2.

EXAMPLE 16

Preparation of the compound (34)

In 30 ml of ethanol was dissolved 966 mg of 5-(3,5-diisopropyl-4-hydroxybenzylidene)-rhodanine, and thereto 726 mg of phenethylamine was added. The mixture was heated under reflux for 12 hours. Ethanol was distilled away under reduced pressure, and the obtained residue was dissolved in chloroform. After washing with water, the solution was subjected to a column-chromatography (carrier: silica-gel) and eluted with chloroform. A fraction containing the desired compound was collected, concentrated, dried and subjected to crystallization to give 600 mg (yield: 68%) of the compound (34).

The melting point and data of elementary analysis of the obtained compound (34) are shown in Table 1. And results of $^1$H-NMR and IR of the obtained compound (34) are shown in Table 2.

EXAMPLE 17

Preparation of the compound (35)

In 30 ml of ethanol was dissolved 966 mg of 5-(3,5-diisopropyl-4-hydroxybenzylidene)-rhodanine, and thereto 773 mg of p-fluorobenzylamine. The mixture was heated under reflux for 7 hours. Ethanol was distilled away under reduced pressure, and the obtained residue was dissolved in chloroform. After washing with water, the solution was subjected to a column-chromatography (carrier: silica-gel) and eluted with chloroform. A fraction containing the desired compound was collected, concentrated and dried to give 660 mg (yield: 52%) of the compound (35).

The melting point and data of elementary analysis of the obtained compound (35) are shown in Table 1. And results of $^1$H-NMR and IR of the obtained compound (35) are shown in Table 2.

EXAMPLE 18

Preparation of the compound (39)

In 30 ml of ethanol was dissolved 966 mg of 5-(3,5-diisopropyl-4-hydroxybenzylidene)-rhodanine, and thereto 726 mg of p-methylbenzylamine was added. The mixture was heated under reflux for 12 hours. Ethanol was distilled away under reduced pressure, and the obtained residue was dissolved in chloroform. After washing with water, the solution was subjected to a column-chromatography (carrier: silica-gel) and eluted with chloroform. A fraction containing the desired compound was collected, concentrated, dried and subjected to crystallization to give 900 mg (yield: 30%) of the compound (39).

The melting point and data of elementary analysis of the obtained compound (39) are shown in Table 1. And results of $^1$H-NMR and IR of the obtained compound (39) are shown in Table 2.

EXAMPLE 19

Preparation of the compound (41)

In 30 ml of ethanol was dissolved 966 mg of 5-(3,5-diisopropyl-4-hydroxybenzylidene)-rhodanine, and thereto 681 mg of p-aminosulfonylbenzylamine hydrochloride and 606 mg of triethylamine. The mixture was heated under reflux for 6 hours. Ethanol was distilled away under reduced pressure, and the obtained residue was dissolved in chloroform. After washing with water, the solution was subjected to a column-chromatography (carrier: silica-gel) and eluted with a mixed solvent of chloroform/ethanol (9/1: v/v). A fraction containing the desired compound was collected, concentrated and dried to give 400 mg (yield: 27%) of the compound (41).

The melting point and data of elementary analysis of the obtained compound (41) are shown in Table 1. And results of $^1$H-NMR and IR of the obtained compound (41) are shown in Table 2.

EXAMPLE 20

Preparation of the compound (42)

In 30 ml of ethanol was dissolved 1.61 g of 5-(3,5-diisopropyl-4-hydroxybenzylidene)-rhodanine, and thereto 1.30 g of p-aminobenzylamine was added. The mixture was heated under reflux for 5 hours. Ethanol was distilled away under reduced pressure, and the obtained residue was subjected to a crystallization from chloroform to give 570 mg (yield: 56%) of the compound (42).

The melting point and data of elementary analysis of the obtained compound (42) are shown in Table 1. And results of $^1$H-NMR and IR of the obtained compound (42) are shown in Table 2.

EXAMPLE 21

Preparation of the compound (44)

In 30 ml of ethanol was dissolved 966 mg of 5-(3,5-diisopropyl-4-hydroxybenzylidene)-rhodanine, and thereto 707 mg of 2-aminomethylthiophene was added. The mixture was heated under reflux for 3 hours. Ethanol was distilled away under reduced pressure, and the obtained residue was dissolved in chloroform. After washing with water, the solution was subjected to a columnchromatography (carrier: silica-gel) and eluted with chloroform. A fraction containing the desired compound was collected, concentrated and dried to give 300 mg (yield: 24%) of the compound (44).

The melting point and data of elementary analysis of the obtained compound (44) are shown in Table 1. And results of $^1$H-NMR and IR of the obtained compound (44) are shown in Table 2.

EXAMPLE 22

Preparation of the compound (45)

In 30 ml of ethanol was dissolved 966 mg of 5-(3,5-diisopropyl-4-hydroxybenzylidene)-rhodanine, and thereto 648 mg of 2-aminomethylpyridine was added. The mixture was heated under reflux for 4 hours. Ethanol was distilled away under reduced pressure, and the obtained residue was dissolved in chloroform. After washing with water, the solution was subjected to a column-chromatography (carrier: silica-gel) and eluted with a mixed solvent of chloroform/ethanol (20/1: v/v). A fraction containing the desired compound was collected, concentrated and dried to give 200 mg (yield: 17%) of the compound (45).

The melting point and data of elementary analysis of the obtained compound (45) are shown in Table 1. And results of $^1$H-NMR and IR of the obtained compound (45) are shown in Table 2.

We claim:

1. A hydroxystyrene derivative represented by the formula (I):

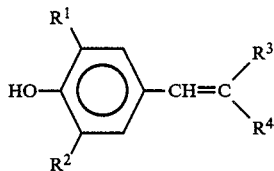

wherein when $R^1$ and $R^2$ are the same or different and each is phenyl group, benzyl group or phenethyl group; or $R^1$ is a group having the formula: $R^5O-$ in which $R^5$ is hydrogen atom, an alkyl group having 1 to 5 carbon atoms or benzyl group, and $R^2$ is benzyl group or a group having the formula $PhSCH_2$, when $R^1$ and $R^2$ are the same or different and each is phenyl group, benzyl group or phenethyl group, or $R_1$ is a group having the formula: $R^5O-$ in which $R^5$ is as defined above, and $R^2$ is benzyl group, $R^3$ is cyano group and $R^4$ is carbamoyl group, or salt thereof.

2. The hydroxystyrene derivative of claim 1, wherein $R^1$ and $R^2$ are the same or different and each is phenyl group, benzyl group or phenethyl group, or $R^1$ is a group having the formula: $R^5O-$ in which $R^5$ is as defined above, and $R^2$ is benzyl group, and $R^3$ is cyano group and $R^4$ is carbamoyl group, or a salt thereof.

3. A tyrosine kinase inhibiting agent containing the hydroxystyrene derivative of claim 1 or a pharmaceutically acceptable salt thereof as an active ingredient.

* * * * *